United States Patent [19]

Pfiffner et al.

[11] 3,983,243

[45] Sept. 28, 1976

[54] EPITHIO COMPOUNDS

[75] Inventors: Albert Pfiffner, Pfaffhausen; Ulrich Schwieter, Reinach, both of Switzerland

[73] Assignee: Hoffmann-La Roche Inc., Nutley, N.J.

[22] Filed: Dec. 11, 1974

[21] Appl. No.: 531,495

Related U.S. Application Data

[60] Division of Ser. No. 68,504, Aug. 31, 1970, Pat. No. 3,883,514, which is a continuation-in-part of Ser. No. 858,534, Sept. 16, 1969, Pat. No. 3,697,543.

[30] Foreign Application Priority Data

| Sept. 27, 1968 | Switzerland | 14522/68 |
| Aug. 29, 1969 | Switzerland | 13141/69 |
| Mar. 25, 1970 | Switzerland | 4619/70 |

[52] U.S. Cl. .............................................. 424/275
[51] Int. Cl.² ........................................ C07D 331/02
[58] Field of Search ................ 260/327 E; 424/275

[56] References Cited

UNITED STATES PATENTS

| 2,419,586 | 4/1947 | Otto et al. ........................ 252/48.2 |
| 3,697,543 | 10/1972 | Pfiffner et al. .................. 260/327 E |
| 3,729,486 | 4/1973 | Siddall et al. ................... 260/327 E |
| 3,755,411 | 8/1973 | Henrick et al. .................. 260/465.6 |

*Primary Examiner*—Henry R. Jiles
*Assistant Examiner*—C. M. S. Taisle
*Attorney, Agent, or Firm*—Samuel L. Welt; George M. Gould; William H. Epstein

[57] ABSTRACT

Epithio unsaturated aliphatic acids, nitriles, and alcohols and ether, ester and amide derivatives thereof and epoxy unsaturated aliphatic acids, nitriles and alcohols and ether ester and amide derivatives thereof, which are useful in killing and preventing proliferation of insects by upsetting their hormone balance.

6 Claims, No Drawings

3,983,243

EPITHIO COMPOUNDS

CROSS REFERENCE TO RELATED APPLICATION

This is a division of application Ser. No. 68,504, filed Aug. 31, 1970, now U.S. Pat. No. 3,883,514, issued May 13, 1975 which is a continuation-in-part of U.S. Patent Application Ser. No. 858,534, filed Sept. 16, 1969, now U.S. Pat. No. 3,697,543, issued Oct. 10, 1972.

SUMMARY OF THE INVENTION

The invention is directed to compounds of the formula:

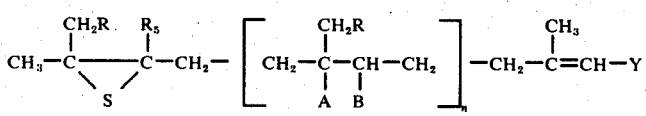

wherein A and B are hydrogen or taken together form a carbon to carbon double bond or a sulfur bridge; R is hydrogen or lower alkyl; $R_5$ is methyl or hydrogen; Y is a member selected from the group consisting of $-C\equiv N$; $-COOR_1$;

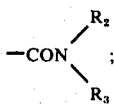

and $-CH_2OR_4$; $R_1$ is selected from the group consisting of hydrogen, phenyl, benzyl, lower alkyl, and substituted phenyl or benzyl; $R_2$ and $R_3$ are hydrogen or lower alkyl, or taken together with their attached nitrogen atom form a 5 or 6 membered heterocyclic ring containing at most one additional hetero atom selected from the group consisting of oxygen, nitrogen or sulfur; $R_4$ is hydrogen, lower alkyl, lower alkanoyl, benzoyl, lower alkyl substituted benzoyl, amino lower alkyl, lower alkyl substituted amino-lower alkyl, benzyl, phenyl, substituted benzyl, substituted phenyl; and n is an integer from 0 to 1;
which are useful in upsetting the hormone balance of pests such as insects.

The compounds of formula I above are prepared by reacting a compound of the formula:

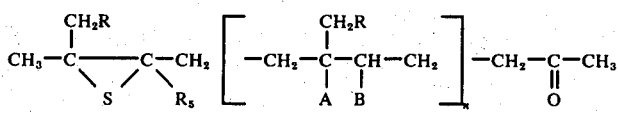

wherein R, $R_5$, A, B and n are as above; with the phosphine oxide of the formula;

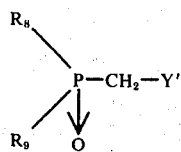

wherein Y' is selected from the group consisting of $-C\equiv N$; $-COOR'_1$; and

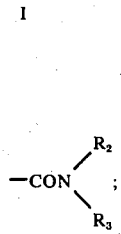

$R'_1$ is lower alkyl, phenyl, benzyl or substituted phenyl and benzyl; $R_8$ and $R_9$ are lower alkoxy or phenoxy, or phenoxy substituted with a radical selected from the group consisting of lower alkoxy, nitro or halo; and $R_2$ and $R_3$, are as above.

In accordance with another embodiment of this invention, compounds of the formula I above are prepared by episulphidizing a compound of the formula:

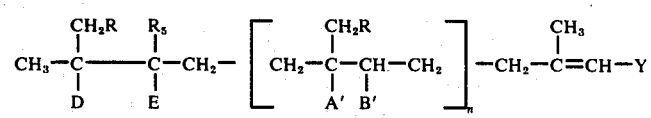

wherein $R_5$, R, Y and n are as above; A' and B' are hydrogen, or taken together form a carbon to carbon double bond or an oxygen bridge; when D is hydroxy, E is halogen or when D is halogen, E is hydroxy, or D and E taken together with D form an oxygen bridge.

If desired, the compound of formula IV above, wherein Y is $-CH_2OH$ and D and E form a sulfur bridge, can be esterified or etherified to form the corresponding ester or ether of formula IV above. The ester can, if desired, be saponified to form the corresponding free alcohol of formula IV above.

In accordance with another embodiment of this invention, we have found that intermediates for compounds of formula I which have the formula:

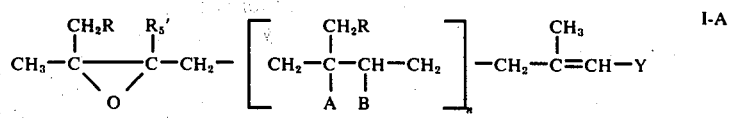

wherein R, Y, A and B, and n are as above, and R₅'
is lower alkyl, preferably methyl and ethyl.
are also useful in upsetting the hormone balance of
pests such as insects.

DETAILED DESCRIPTION OF THE INVENTION

As used throughout the application, the term "lower alkyl" comprehends both straight and branched chain saturated hydrocarbon groups containing from 1 to 6 carbon atoms such as methyl, ethyl, propyl, isopropyl, etc. The term "lower alkoxy" comprehends lower alkoxy groups containing from 1 to 6 carbon atoms such as When, in the compound of formulae I or I-A above, $R_2$ and $R_3$ form a 5 or 6 membered heterocyclic ring, with their attached nitrogen atom, the ring can contain an additional heteroatom such as nitrogen, oxygen or sulfur. Among the preferred 5 or 6 membered heterocyclic ring moieties formed by $R_2$ and $R_3$ taken together with their attached nitrogen atom are included pyrrolidino, piperidino and morpholino.

When $R_1$, in the compound of formula I above is a substituted or unsubstituted phenyl or benzyl, in accordance with a preferred embodiment of the invention, the compound of formula I has the formula:

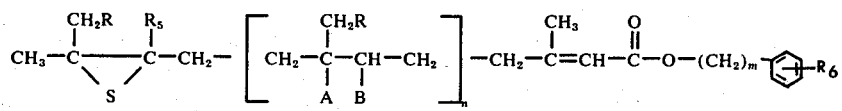

methoxy, propoxy, ethoxy, etc. The term "lower alkoxy carbonyl" as used throughout this application, comprehends lower alkoxy carbonyl groups wherein the lower alkoxy substituent contains from 1 to 6 carbon atoms. Examples of lower alkoxy carbonyl groups are methoxy-carbonyl, ethoxy-carbonyl and isopropoxy-carbonyl with the methoxy-carbonyl and ethoxy-carbonyl wherein $n$, R, $R_5$, A, and B are as above; $R_6$ is lower alkyl, hydroxy, lower alkoxy, hydrogen or halogen, and $m$ is an integer of from 0 to 1.

When $R_4$, in the compound of formula I above is a substituted or unsubstituted benzyl or phenyl, a preferred embodiment of the compound of formula I above has the following formula:

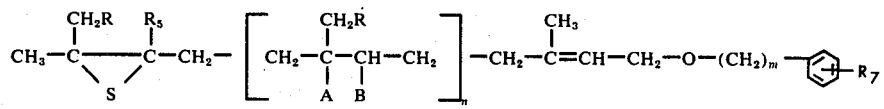

groups being preferred.

The term "lower alkyl-substituted amino lower alkyl" groups as used throughout this application comprehends both monolower alkyl substituted amino lower alkyl groups and dilower alkyl substituted amino lower alkyl groups wherein the lower alkyl moiety or moieties contain from 1 to 6 carbon atoms. Among the preferred lower alkyl substituted amino alkyl groups are monomethylamino-methyl, dimethylamino-ethyl, monoethylamino-propyl, diethylamino-methyl, monoisopropylamino-propyl, and diisopropylaminowherein R, $R_5$, A, B, $n$, and $m$ are as above; and $R_7$ is lower alkyl, lower alkoxy, hydrogen, methylenedioxy, lower alkoxy carbonyl, phenyl lower alkyl, lower alkanoyl, halogen, benzoyl, and lower alkyl benzoyl.

When $R_4$ and $R_7$ are lower alkyl benzoyl, the preferred radicals are toluyl and p-ethyl benzoyl.

When $R_1$ in the compound of formula I-A is a substituted or unsubstituted phenyl or benzyl, in accordance with a preferred embodiment of the invention, the compound of formula I-A has the formula:

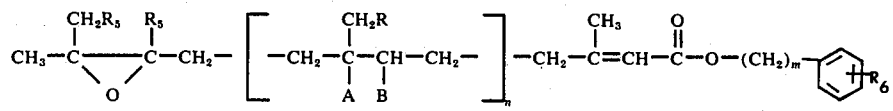

ethyl. As used in this application, the term "halogen" includes all four halogens such as bromine, chlorine, fluorine and iodine with fluorine, chlorine and bromine being preferred. The term "lower alkanoyloxy" as used throughout the specification includes lower alkanoyloxy groups containing from 1 to 6 carbon atoms such as acetyloxy, formyloxy, propionyloxy, butyryloxy, etc.

The term "methylenedioxy" is represented by the formula —O—CH₂—O—, and can be connected to two adjacent carbon atoms on the benzene moiety.

wherein $n$, $m$, R, $R_5$, A and B, and $R_6$ are as above.

When $R_4$ in the compound of formula I-A is a substituted phenyl or benzyl, in accordance with a preferred embodiment of the invention, the compound of formula I-A has the formula:

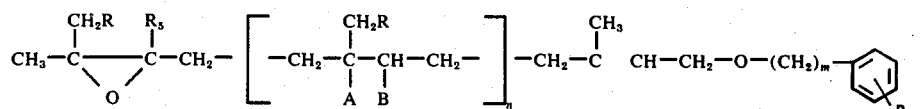

wherein A, B, $n$, $m$, R, $R_5$ and $R_7$ are as above.

The compounds of formulae I and I-A above are useful in the control of pests such as insects which include *Tenebrio molitor* (yellow mealworm), *Tineola biselliella* (clothes moth), *Carpocapsa pomonella* (codling moth), *Leptinotarsa decemlineata* (Colorado beetle), *Calandra granaria* (grain weevil), *Dysdercus cingulatus* or *Ephestia kuhniella*, etc. In contrast to most of the known pest-control agents which kill, disable or repell the pests by acting as contact-poisons and feed-poisons, the compounds of formula I and formula I-A above and said mixtures thereof prevent maturation and proliferation of these pests by upsetting their hormone balance. In insects, for example, the transformation into the imago is disturbed. Furthermore, the sequence of generations is interrupted and the insects are indirectly killed.

The compounds of formulae I and I-A above are practically non-toxic to vertebrates. The toxicity of these compounds in vertebrates is greater than 1,000 mg/kg body weight. Moreover, these compounds are readily degraded and the risk of accumulation is therefore excluded. Therefore, these compounds can be used without fear or danger in the control of pests in animals, plants, foods and textiles.

Generally, in controlling invertebrate animals, the compounds of formulae I and I-A above are applied to the material to be protected, e.g., foodstuffs, feeds, textiles, plants in an amount of from about 0.01 percent to 0.1 percent by weight of the material to be protected. Generally, it is preferred to utilize the compounds of formulae I or I-A above in a composition with a suitable inert carrier. Any conventional inert carrier can be utilized. The composition which contains an effective amount of the compounds of formulae I or I-A above should be applied to the material to be protected to provide a concentration of from about 0.01 percent to 0.1 percent of the compound of formula I above on said material.

The compounds of formulae I and I-A above can, for example, be used in the form of emulsions, suspensions, dusting agents, solutions or aerosols. In special cases, the materials to be protected (e.g., foodstuffs, seeds, textiles and the like) can also be directly impregnated with the appropriate compound or with a solution thereof. Moreover, the compounds can also be used in a form which only releases them by the action of external influences (e.g., contact with moisture) or in the animal body itself.

The compounds of formula I and I-A above can be used as solutions suitable for spraying on the material to be protected which can be prepared by dissolving or dispersing these compounds in a solvent such as mineral oil fractions; cold tar oils; oils of vegetable or animal origins; hydrocarbons such as naphthalenes ketones such as methyl ethyl ketone; or chlorinated hydrocarbons such as tetrachloroethylene, tetrachlorobenzene, and the like. The compounds of formula I and I-A above can also be prepared in forms suitable for dilution with water to form aqueous liquids such as, for example, emulsion concentrates, pastes or powders.

The compounds of formula I and I-A above can be combined with solid carriers for making dusting or strewing powders as, for example, talc, kaolin, bentonite, calcium carbonate, calcium phosphate, etc. The compositions containing the compound of formula I above can contain, if desired, emulsifiers, dispersing agents, wetting agents, or other active substances such as fungicides, bacteriacides, nematocides, fertilizers and the like.

Among the compounds of formula I which are especially suited for killing and preventing the proliferation of insects are included:
 (6,7-epithio-3,7-dimethyl-2-octenyl) methyl ether;
 6,7-epithio-3,7-dimethyl-2-octenoic acid ethyl ester;
 (10,11-epithio-3,7,11-trimethyl-2,6-dodecadienyl) methyl ether;
 (α-phenyl-p-tolyl) (10,11-epithio-3,7,11-trimethyl-2-cis/trans,6-cis-dodecadienyl) ether;
 (10,11-epithio-7-ethyl-3,11-dimethyl-2,6-tridecadienyl) methyl ether;
 10,11-epithio-N,N-diethyl-3,7,11-trimethyl-2,6-dodecadienoic acid amide;
 10,11-epithio-3,7,11-trimethyl-2,6-dodecadienoic acid ethyl ester;
 10,11-epithio-3,7,11-trimethyl-2,6-tridecadienoic acid ethyl ester;
 10,11-epithio-7-ethyl-3,11-dimethyl-2,6-tridecadienoic acid ethyl ester;
 10,11-epithio-3,7,10,11-tetramethyl-2,6-dodecaidenoic acid ethyl ester; and
 10,11-epithio-3,7,11-trimethyl-2,6-dodecadiene nitrile.

Among the compounds of formula I-A which are especially suited for killing and preventing proliferation of insects are included:
 (10,11-epoxy-3,7,10,11-tetramethyl-dodeca-2,6-dienyl)methyl ether;
 10,11-epoxy-N,N-diethyl-3,7,10,11-tetramethyl-2,6-dodecadienoic acid amide;
 10,11-epoxy-3,7,10,11-tetramethyl-dodeca-2,6-dienoic acid ethyl ester;
 10,11-epoxy-3,7,10,11-tetramethyl-dodeca-2,6-dienenitrile; or
 6,7-epoxy-3,6,7-trimethyl-1-[3,4-methylenedioxy)-phenoxy]-2-octene.

Among the compounds of formula II which are produced in accordance with this invention are included:
 5,6-epithio-6-methyl-heptan-2-one;
 9,10-epithio-6,10-dimethyl-undec-5-en-2-one;
 9,10-epithio-6,10-dimethyl-dodec-5-en-2-one;
 9,10-epithio-6-ethyl-10-methyl-dodec-5-en-2-one; and
 9,10-epithio-6,9,10-trimethyl-undec-5-en-2-one.

Compounds of formula II above can be prepared via the following reaction scheme:

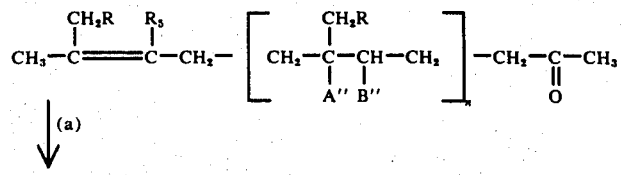

-continued

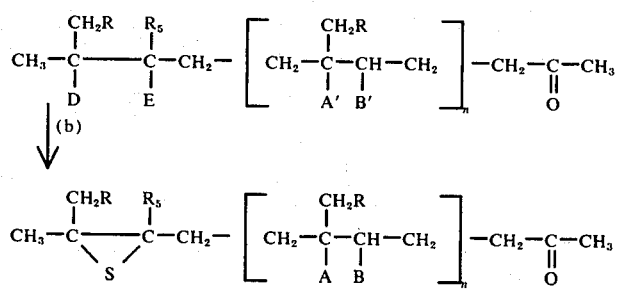

wherein R, n, R$_5$, and A' and B' and B and D and E are as above; and A'' and B'' are hydrogen or taken together form a carbon to carbon double bond.

In accordance with this invention, in step (a) the compound of formula V above can be converted to the compound of the formula VI above by either treating the compound of formula V above with an N-halosuccinimide and water or by treating the compound of formula V with organic peracids. The treatment of the compound of formula V with an N-halosuccinimide and water selectively and exclusively oxidizes the terminal double bond giving rise to the halohydrins of formula VI, i.e., wherein D is hydroxy and E is halogen. On the other hand, when the compound of formula V above where A'' and B'' form a carbon to carbon double bond, is epoxidized with an organic peracid, epoxidation of one or more of the double bonds within the compound of formula V can be carried out depending upon the conditions utilized.

The compound of formula V is converted into the compound of formula VI wherein D is hydroxy and E is halogen by treating the compound of formula V with an N-halosuccinimide preferably N-bromosuccinimide and water to selectively and exclusively oxidize the terminal bond giving rise to the corresponding halohydrins. The formation of these halohydrins is carried out at a temperature of from 0° to 30°C. The use of N-halosuccinimide and water to hydroxyhalogenate the compounds of formula V selectively hydroxy-halogenates the terminal double bond without affecting any other double bond. An inert organic solvent can be added in addition to the water. Any conventional inert organic solvent can be utilized with tetrahydrofuran being the preferred solvent.

If desired, the halohydrin of formula VI above can be converted into the corresponding epoxy compound by treating the halohydrin with a base. This reaction is preferably carried out in the same reaction medium that was utilized to form the halohydrin. The formation of the oxide from the halohydrin is carried out at a temperature of from 0° to 30°C. Any of the conventional bases such as an alkali metal, alkali metal hydroxide, an alkali metal alcoholate such as sodium methylate, sodium ethylate, etc. can be utilized to convert the compound of formula VI wherein D is hydroxy and E is halogen to the compound of formula VI wherein D and E form an oxygen bridge.

The halohydrin compound of formula VI where A' and B' form a carbon to carbon bond can be converted to the halohydrin compound of formula VI where A' and B' form an oxygen bridge by treating the compound of formula VI with an organic peracid in the manner mentioned hereinafter. In this manner a compound of formula VI is produced wherein D is hydroxy, E is a halogen and A' and B' form an oxygen bridge.

The compound of the formula V above is converted to the epoxide of formula VI, i.e., where D and E and/or A' and B' form an oxygen bridge by treating the compound of formula V with an organic peracid. Any conventional organic peracid can be utilized in this reaction. Among the conventional organic peracids which can be utilized are included peracetic acid, perbenzoic acid, 3-chloroperbenzoic acid and perphthalic acid. This reaction is usually carried out in an inert organic solvent. Any conventional inert organic solvent can be utilized. Among the inert organic solvents which can be utilized, the halogenated hydrocarbons such as methylene chloride and chloroform are preferred. Generally, this reaction is carried out at a temperature of from about 0° to 30°C.

The use of about 1 mole of an organic peracid per mole of the compound of formula V wherein A'' and B'' form a carbon to carbon double bond produces a mixture of the compound of formula VI wherein D and E form an oxygen bridge and the compound of formula VI wherein A' and B' form an oxygen bridge. These isomers can be separated by conventional means such as fractional distillation. If it is desired to epoxidize all of the double bonds in a compound of formula V above wherein A'' and B'' form a double bond, one mole of the compound of formula V is epoxidized in the foregoing manner with at least the number of moles of the organic peracid per double bond contained within one mole of the compound of the formula V.

The compound of formula VI can be episulphidized to the compound of formula II by any conventional means. When the compound of formula VI is a halohydrin, i.e., D is hydroxy and E is halogen, the compound of formula VI is episulphidized in a two-step process. In the first step the halohydrin of formula VI above is reacted with an episulphidizing agent to form the isothiouronium salt. The isothiouronium salt is then cleaved with a base to form the epithio compound of the formula II above.

The conversion of the halohydrin compound of formula VI above to the isothiouronium salt is carried out by utilizing an episulphidizing agent. Any conventional episulphidizing agent can be utilized in carrying out this reaction step. Among the conventional episulphidizing agents are included thiocyanates such as ammonium thiocyanate; alkali metal thiocyanates such as sodium thiocyanate or potassium thiocyanate; thiourea; N-substituted thiourea such as thiobarbituric acid; thioamides; or alkali metal thiosulfates such as sodium thiosulfates. Of the episulphidizing agents, thiourea and alkali metal thiocyanates are preferred. Generally, in carrying out this reaction at least one mole of the episulphidizing agent is present per mole of the halohydrin of formula VI. The formation of the isothiouronium salt from the halohydrin of formula VI above is generally carried out in the presence of an inert polar organic solvent. Any conventional polar organic solvent can be utilized. Among the conventional organic polar solvents which can be utilized in this conversion, lower alkanols such as methanol is preferred. In carrying out this reaction temperature and pressure are not critical and this reaction can be carried out at room temperature and at atmospheric pressure. However, if desired, temperatures as high as the reflux temperature of the reaction mixture can be utilized.

The isothiouronium salt is cleaved to form the epithio compound of formula II by treating the isothiouronium salt with a base. Any of the conventional bases such as those hereinbefore mentioned can be utilized. Among the conventional bases which can be utilized, alkali metal carbonates such as sodium carbonate and potassium carbonate are preferred. Generally, these carbonates are added in the form of an aqueous solution. Generally, this cleavage of the isothiouronium salt is carried out in the solvent system which was utilized for its formation. Therefore, organic polar solvents such as methanol and ethanol are preferred. In carrying out this cleavage reaction, temperature and pressure are not critical and this reaction can be carried out at room temperature and atmospheric pressure. However, higher or lower temperatures can be utilized. Any temperatures of from about 0°C. to the reflux temperature of the reaction mixture are utilized. However, temperatures of from 0°C. to 5°C. are generally preferred.

The epithio compound of formula II which is formed can be extracted from the reaction medium by any conventional means such as with an ether. If necessary, the crude product can be purified, for example by chromatographing on Kieselgel.

The epoxy compound of formula VI above wherein either D and E or both D and E and A' and B' form oxygen bridges can be converted to the epithio compound of formula II above by epi sulphidization by any one of two methods. In the first method the epoxide of formula VI is converted to the compound of formula II above in two steps. In the first step the epoxide of formula VI above is reacted with an episulphidizing agent in the presence of a mineral acid at a temperature of from 0°C. to 30°C. to form the isothiouronium salt. In the second step the isothiouronium salt is cleaved to form the epithio compound of formula II by means of treatment with a base.

In the first step of this reaction, the epoxide of formula VI is reacted with an episulphidizing agent in the presence of a mineral acid at a temperature of from 0° to 30°C. Generally it is preferred to utilize temperatures of from 0° to 5°C. in carrying out this reaction. Any conventional mineral acid can be utilized such as sulphuric acid, hydrochloric acid, etc. The preferred acid is an aqueous sulphuric acid such as 2N aqueous sulphuric acid. Any conventional episulphidizing agent such as the episulphidizing agents mentioned hereinbefore can be utilized. Thiourea is the preferred episulphidizing agent. Generally in carrying out this reaction at least one mole of the episulphidizing agent is present per epoxy group contained within a mole of the compound of formula VI. In carrying out this reaction, an inert organic solvent can be utilized. Any conventional inert organic solvent can be utilized. Among the inert organic solvents, dioxane is preferred. The thiouronium salt thus formed can be converted into the compound of formula II above in the manner hereinbefore described.

On the other hand, the epoxide of formula VI can be converted into the compound of formula II in one step by reacting the epoxide of formula VI with an episulphidizing agent at the reflux temperature of the reaction medium. This one-step reaction can be carried out without the presence of a mineral acid. Any conventional episulphidizing agent such as the agents mentioned hereinbefore can be utilized in carrying out this one-step reaction. However, among the preferred episulphidizing agents are included the alkali metal thiocyanates such as sodium or potassium thiocyanate and thiourea. Generally in carrying out this reaction at least one mole of the episulphidizing agent is utilized per epoxide group contained within one mole of the compound of formula VI. Furthermore, this reaction is generally carried out in a solvent medium. Any conventional inert organic solvent such as the solvents hereinbefore mentioned can be utilized in carrying out this reaction. Among the preferred solvents are included lower alkanols such as ethanol and methanol.

In the case where both D and E and A' and B' in the compound of formula VI above form oxygen bridges both of the oxygen bridges are episulphidized by the aforementioned process. However in the case where only D and E form an oxygen bridge and A' and B' are hydrogen or a double bond in the compound of formula VI above, only the oxygen bridge formed by D and E is episulphidized.

In accordance with this invention, the compounds of formula II above are converted to the compounds of formula I above wherein Y is -CN, -COOR$_1$' and

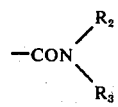

by reacting the compound of the formula II above with a phosphine oxide of formula III above. Generally this reaction is carried out in the presence of an alkali metal base in an inert organic solvent. Any conventional alkali metal base can be utilized. Among the conventional alkali metal bases are included alkali metal hydrides such as sodium hydride, potassium hydride; alkali metal lower alkoxides, such as sodium methoxide, sodium ethoxide, etc.; and the alkali metal amide bases such as sodamide, potassium amide, sodium methyl amide, potassium methyl amide, as well as other alkali metal lower alkyl amides. In carrying out this reaction, any inert organic solvent can be utilized, such as benzene, toluene, N,N-dimethylformamide, tetrahydrofuran, dioxane, 1,2-dimethoxyethane. In carrying out this reaction, the temperature of from 0°C. to 30°C. should be utilized.

Among the compounds of formula IV above which are utilized in accordance with this invention are included:
10,11-epoxy-1-ethoxy-3,7,11-trimethyl-2,6-dodecadiene;
3-bromo-12-methoxy-2,6,10-trimethyl-6,10-dodecadien-2-ol;
10,11-epoxy-1-methoxy-3,7,11-trimethyl-2,6-dodecadiene;

10,11-epoxy-1-methoxy-3,7,11-trimethyl-2,6-tridecadiene;
10,11-epoxy-1-methoxy-3,7,10,11-tetramethyl-2,6-dodecadiene;
10,11-epoxy-3,7,11-trimethyl-2,6-dodecadiennitrile;
10-bromo-11-hydroxy-3,7,11-trimethyl-2,6-dodecadienoic acid ethyl ester;
10,11-epoxy-3,7,11-trimethyl-2,6-tridecadienoic acid ethyl ester;
10,11-epoxy-7-ethyl-3,11-dimethyl-2,6-tridecadienoic acid ethyl ester;
10,11-epoxy-3,7,10,11-tetramethyl-2,6-dodecadienoic acid ethyl ester;
10,11-epoxy-N,N-diethyl-3,7,11-trimethyl-2,6-dodecadienoic acid amide.

When Y in the compound of formula IV above is —C≡N; —COOR'₁ or

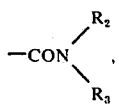

this compound can be prepared by the following reaction scheme:

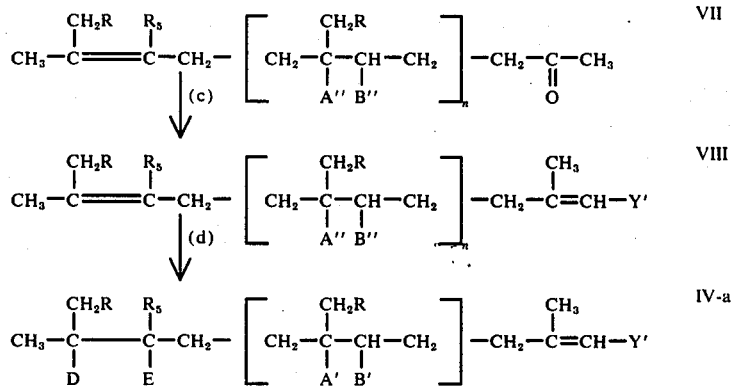

wherein Y', A' and B', A'' and B'' and D and E are as above.

The compound of formula VII is converted to the compound of formula VIII by reaction with a phosphine oxide of formula III above in the same manner described in connection with the conversion of compounds of the formula II into compounds of the formula I above. The compound of the formula VIII above is converted to a compound of the formula IV-a above by either treatment with an organic peracid to epoxidize the terminal double bond and the double bond formed by A'' and B'' or by hydroxy halogenation to convert the terminal double bond of the compound of the formula VIII into a halohydrin group. The same conditions that were described in connection with step (a) are utilized in carrying out the reaction of step (d). The compound of the formula IV-a can be converted to the compound of the formula I wherein Y is Y' by episulphidizing the compound of the formula IV-a in the manner described in connection with step (b).

Where Y' is —COO lower alkyl in the compounds of formulae VIII, IV-a or I above, these compounds can be converted to the free acid by any conventional technique of ester hydrolysis or saponification such as treatment with an alkali, i.e., sodium hydroxide, potassium hydroxide, etc.

The free acids of formula VIII can be converted to the corresponding acid amides, i.e., where Y' is

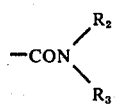

first converting the acid to an acid chloride and then reacting the acid chloride with an amine of the formula:

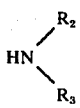         XX wherein R₂ and R₃ are as above.

Any of the conditions conventional in converting a free acid to an acid halide can be utilized in this reaction such as by treating the free acid with a halogenating agent such as thionyl chloride in the presence of a base such as pyridine. The acid halide is converted to the compound of formulae I and IV-a above wherein Y is

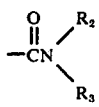

by reacting the acid halide with an amine of the formula XX. Any conventional means for converting acid halides to acid amides can be utilized.

On the other hand, the acid halide can be converted to an ester by reacting the acid halide with an alkali metal alcoholate of the formula:

R₁' - O - M                   XXI wherein R₁' is as above and M is the alkali metal. Any of the conditions conventional in reacting alkali metal alcoholates with acid halides to form esters can be utilized.

This reaction scheme can be exemplified as follows. Geranyl acetone is condensed in an ethanolic solution with, for example, a dialkyl phosphonoacetic acid ester in the presence of sodium in absolute ethanol. The 3,7,11-trimethyl-2-cis/trans-6-trans-10-dodecatrienoic acid ethyl ester is saponified to the corresponding free acid with an aqueous ethanolic caustic soda solution. The free acid which is obtained can be converted into the acid chloride by any conventional method such as with thionyl chloride in the presence of pyridine. The acid chloride by reaction with an amine of the formula XX can be transformed into an acid amide.

On the other hand, the acid halide can be reacted with an alcohol or alcoholate of the formula XXI to produce an ester. On the other hand, the 3,7,11-trimethyldodeca-2-cis/trans-6-trans-10-trienoic acid ethyl ester can be converted into a bromohydrin. In this process, the ester is dissolved in water/tetrahydrofuran and gradually treated at low temperatures (preferably at 0° to 5°C.) with N-bromosuccinimide. The reaction mixture can then be stirred in the cold for about six hours. After this period, it is then treated with a saturated aqueous sodium chloride solution and extracted with hexane. The 10-bromo-11-hydroxy-3,7,11-trimethyl-dodeca-2-cis/trans-6-trans-dienoic acid ethyl ester recovered from the extract can, if desired, be purified by chromatography on Kieselgel.

The bromohydrin can be converted into the corresponding epoxide by first dissolving the bromohydrin in absolute ethanol. This solution is treated dropwise in the cold, generally at about 0°C., with a solution of sodium and absolute ethanol. The reaction mixture is stirred for about 1 hour, then poured into a concentrated aqueous common salt solution and preferably extracted with hexane. From the extract, 10,11-epoxy-3,7,11-trimethyl-dodeca-2-cis/trans-6-trans-dienoic acid ethyl ester is obtained, which can be purified by rectification.

The alcohol and esters thereof of formula I which have the formula:

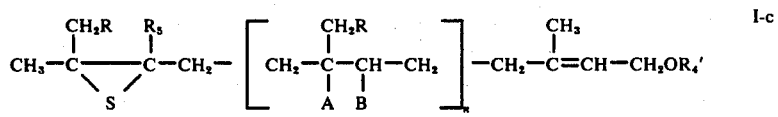

wherein R, $R_5$, A, B and n are as above, and $R_4'$ is lower alkyl, lower alkanoyl, benzoyl, lower alkyl substituted benzoyl, amino lower alkyl, lower alkyl substituted amino, benzyl, phenyl, substituted benzyl, and substituted phenyl, can be prepared from an alcohol of the formula:

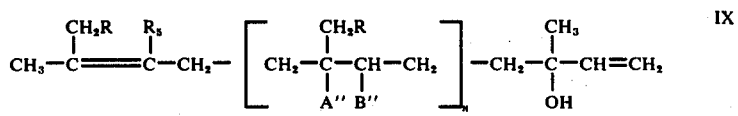

wherein A'' and B'', R, $R_5$ and n are as above, by the following reaction scheme:

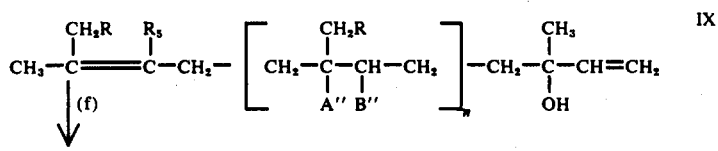

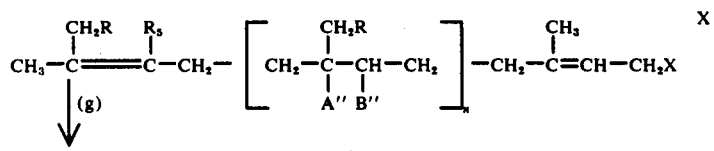

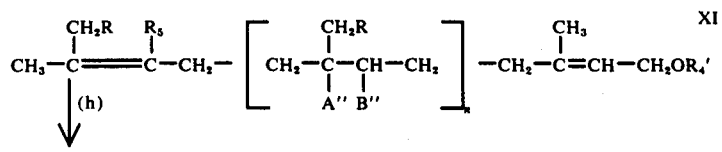

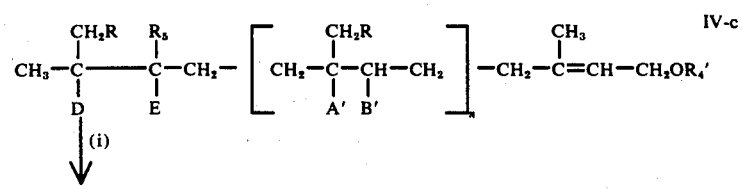

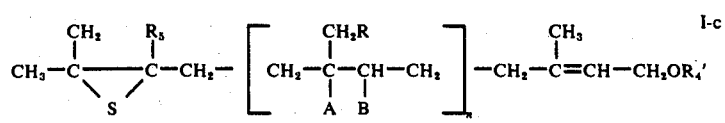

wherein A′ and B′, A″ and B″, A and B, D and E, R, R$_5$, R$_4$′ and $n$ are as above, and X is a halogen.

The compound of formula IX above is converted to the compound of formula X above via reaction step (f) by subjecting the compound of formula IX above to halogenation in the presence of a base. Any conventional method of halogenation can be utilized in carrying out the reaction of step (f). Generally, the halogenation can be carried out by treating the compound of formula IX above with a halogenating agent such as a thionyl halide or a phosphorous trihalide in the presence of a base. Among the preferred halogenating agents are included phosphorous tribromide, phosphorous pentachloride, thionyl chloride, etc. Any conventional base such as the bases mentioned hereinbefore can be utilized in carrying out this reaction. Among the preferred bases are included the tertiary amines such as pyridine. In carrying out this reaction, an inert organic solvent medium is generally utilized. Any conventional inert organic solvent such as hexane or ether can be utilized. Furthermore, this reaction is generally carried out at a temperature of from about −15°C to 30°C.

The compound of formula X can be converted to the compound of formula XI by reacting the compound of formula X with a compound of the formula:

$$MO - R_4'  \qquad XXII$$

wherein M is an alkali metal such as potassium, sodium, lithium, etc. and R$_4$′ is as above. Any of the conditions conventional in reacting alkali metal alcoholates or alkali metal alkanoates with primary halides can be utilized in carrying out this reaction.

The reaction of step (h) wherein the compound of formula XI above is converted into the compound of formula IV-c above is carried out by either the epoxidation technique or the halohydrin technique described in connection with step (a). The conversion of compounds of the formula IV-c into compounds of the formula I-c is carried out by the episulphidization technique described in connection with step (b).

The compounds of the formula I-c wherein R$_4$′ is lower alkanoyl, benzoyl or lower alkyl substituted benzoyl, can be converted by saponification to the free alcohol, i.e., where R$_4$′ is hydrogen by ester saponification. Any conventional method of ester saponification can be utilized in converting such compounds to the free alcohol.

The free alcohol of formula I-c above can be converted into the corresponding alkali metal salt by treating this free alcohol with an alkali metal base in the presence of an inert organic solvent. Any conventional alkali metal base can be utilized in this conversion. Among the bases that can be utilized are included potassium tertiary butylate, alkali metals, alkali metal hydrides, preferably sodium hydride. In carrying out this reaction, any conventional inert organic solvent can be utilized. Among the inert organic solvents which can be utilized are included benzene, toluene, dimethyl formamide, dioxane, dimethoxy ethane. In carrying out this reaction, temperature and pressure are not critical and this reaction can be carried out at room temperature and atmospheric pressures. However, if desired, lower or higher temperatures can be utilized.

The alkali metal salts prepared above can be converted to the corresponding ethers by etherification with an alkyl or aryl or aralkyl halide. The halide group is preferably an iodine or bromine group. This etherification reaction can be carried out in any of the inert solvents mentioned above. Preferably, this reaction is carried out in an aprotic solvent such as hexamethyl phosphoric acid triamide. Furthermore, in carrying out this reaction temperatures and pressures are not critical and this reaction can be carried out at room temperature and atmospheric pressure. Alternatively, this reaction can be carried out at higher or lower temperatures, generally this reaction is carried out at a temperature of from about 0°C. to the reflux temperature of the reaction mixture.

Alternatively, the free alcohols of the formula I-c, i.e., where R$_4$′ is H, can be esterified. This esterification reaction can be carried out in the same manner described above in connection with the etherification reaction. However, in the esterification reaction, the lower alkanoic, lower aroyl, lower aralkanoic acid is utilized. The acid can be in its derivative form such as its anhydride or acid halide forms. In the esterification reaction, there is no need to convert the free alcohol starting material of formula I-c to its alkali metal salt. If the conversion of the alcohol to the alkali metal salt is omitted, the reaction of the alcohol of formula I-c is carried out with an acylating agent in the presence of an acid binding agent. Any conventional acid binding agent such as pyridine and triethylamine can be utilized in carrying out this reaction.

The following examples are illustrative but not limitative of this invention. The ether utilized in these examples was diethyl ether. The temperature in all of these examples is in degrees Centigrade.

EXAMPLE 1

33.3 g. of 3-bromo-12-methoxy-2,6,10-trimethyl-dodecadien-2-ol [cis and trans mixture] are heated under reflux conditions for 1 hour together with 7.6 g. of thiourea and 150 ml. of absolute ethanol. The reaction mixture is cooled to 40°C., after the addition of 6.9 g. of potassium carbonate in 25 ml. of water, stirred for 2 hours and subsequently concentrated under reduced pressure. The concentrate is taken up with water and exhaustively extracted with ether. The extract is washed with a saturated aqueous sodium chloride solution, dried over sodium sulfate and evaporated. The residual (10,11-epithio-3,7,11-trimethyl-2,6-cis/trans-dodecadienyl) methyl ether is purified by chromatographing on Kieselgel [eluting agent hexane-acetic acid ethyl ester (80:20 parts by volume)], b.p. 97°–98°C./0.025 mm Hg; n$_D^{20}$ = 1.5016.

EXAMPLE 2

7.3 g. of 10,11-epoxy-1-methoxy-3,7,11-trimethyl-2-cis/trans, 6-cis-dodecadiene are added dropwise at 0°–5°C. with strong stirring to a suspension of 2.15 g. of thiourea in 14 ml. of 2-N-sulfuric acid. The reaction mixture is further stirred for 2.5 hours at 0°–5°C., then treated with 1.5 g of sodium carbonate in 5.5 ml. of water and heated under reflux conditions for 2 hours. The mixture is subsequently cooled, diluted with water and exhaustively extracted with ether. The extract is washed with a saturated aqueous sodium chloride solution, dried over sodium sulfate and evaporated. The residual (10,11-epithio-3,7,11-trimethyl-2-cis/trans, 6-cis-dodecadienyl) methyl ether is purified by chromatographing on Kieselgel [eluting agent hexane-acetic acid ethyl ester (60:40 parts by volume)], b.p. 95°–96°C./0.01 mm Hg; n$_D^{20}$ = 1.5022.

EXAMPLE 3

To a suspension of 2.3 g. of finely pulverized thiourea in 15.1 ml. of 2-N sulfuric acid, 8 g. of (10,11-epoxy-3,7,11-trimethyl-2,6-tridecadienyl) methyl ether was added dropwise under constant stirring while cooling with ice. The resulting mixture was allowed to stand for 2 hours under constant mixing while cooling with ice. After this period, a solution containing 1.6 g. of sodium carbonate in 6 ml. of water were added dropwise to the reaction mixture while it stood for 1 hour at room temperature. The reaction mixture was poured into water and exhaustively extracted with diethyl ether. The extract was washed with a saturated aqueous sodium chloride solution, dried over sodium sulfate and evaporated. The residual (10,11-epithio-3,7,11-trimethyl-2,6-tridecadienyl) methyl ether was purified by chromatographing on Kieselgel [eluting agent hexane/ethyl acetate (4:1 parts by volume)], b.p. 110°C./0.001 mm Hg, (bulb tube distillation); $n_D^{20}$ = 1.5008.

By the same procedure, (10,11-epoxy-7-ethyl-3,11-dimethyltrideca-2,6-dienyl) methyl ether was converted to (10,11-epithio-7-ethyl-3,11-dimethyl-trideca-2,6-dienyl) methyl ether and (10,11-epoxy-3,7,10,11-tetramethyl-dodeca-2,6-dienyl) methyl ether was converted to (10,11-epithio-3,7,10,11-tetramethyl-dodeca-2,6-dienyl) methyl ether.

EXAMPLE 4

3 g. of 10,11-epoxy-3,7,11-trimethyl-1-[(p-benzyl phenyl)-oxy]-2-cis/trans, 6-cis-dodecadiene are mixed together with 5.65 g. of thiourea, 17 ml. of dioxan and 3.7 ml. of 2-N sulfuric acid. The homogeneous solution is allowed to stand in the cold (ca 0°) for 8 hours. It is subsequently treated with 390 mg. of sodium carbonate in 1.5 ml. of water, stirred at room temperature for 3 hours, then diluted with water and exhaustively extracted with acetic acid ethyl ester. The extract is washed several times with a saturated aqueous sodium chloride solution, dried over sodium sulfate and evaporated. The residual (p-benzyl phenyl) (10,11-epithio-3,7,11-trimethyl-2-cis/trans, 6-cis-dodecadienyl) ether can be purified by chromatographing on Kieselgel [eluting agent hexane-acetic acid ethyl ester (80:20 parts by volume)], $n_D^{20}$ = 1.5639.

The 10,11-epoxy-3,7,11-trimethyl-1-[(p-benzyl phenyl)-oxy]-2-cis/trans, 6-cis-dodecadiene employed as the starting compound can, for example, be manufactured as follows:

28.5 g. of 2-cis/trans, 6-cis-farnesyl bromide are added dropwise within 15 minutes at room temperature with stirring to a mixture of 20.2 g. of p-benzyl phenol, 20.8 g. of potassium carbonate and 100 ml. of acetone. The reaction mixture is heated under reflux conditions for 12 hours and subsequently concentrated. The concentrate is poured into 600 ml. of ice-water and exhaustively extracted with hexane. The extract is washed in 1-N caustic soda and subsequently neutral with a saturated aqueous sodium chloride solution, dried over sodium sulfate and evaporated. The residual (p-benzyl phenyl) (3,7,11-trimethyl-2-cis/trans,6-cis,10-dodecatrienyl)ether can be purified by chromatographing on Kieselgel [eluting agent hexane-acetic acid ethyl ester (98:2 parts by volume)], b.p. 195°–200°C./0.005 mm Hg.

7.21 g of N-bromosuccinimide are introduced within 20 minutes at 1°–3°C. while gassing with argon into a mixture of 15.0 g. of (p-benzyl phenyl) (3,7,11-trimethyl-2-cis/trans, 6-cis,10-dodecatrienyl) ether, 16 ml. of water and 90 ml. of tetrahydrofuran. The reaction mixture is stirred at 0°–3°C. for 5 hours, then poured into 100 ml. of ice-water and exhaustively extracted with hexane. The extract is washed with a saturated aqueous sodium chloride solution, dried over sodium sulfate and evaporated under reduced pressure. The residual 3-bromo-2,6,10-trimethyl-12-[(p-benzyl phenyl)-oxy]-6-cis,10-cis/trans-dodecadien-2-ol is purified by chromatographing on Kieselgel [eluting agent hexane-acetic acid ethyl ester (90:10 parts by volume)].

9.2 g. of 3-bromo-2,6,10-trimethyl-12-[(p-benzyl phenyl)oxy]-6-cis,10-cis/trans-dodecadien-2-ol in 40 ml. of methanol are treated dropwise within 15 minutes at 1°–3°C. with a solution of 0.44 g. of sodium in 10 ml. of methanol. The reaction mixture is stirred at 1°–3°C. for 30 minutes, then poured into 100 ml. of ice-water and exhaustively extracted with hexane. The extract is dried over sodium sulfate and evaporated under reduced pressure. The residual 10,11-epoxy-3,7,11-trimethyl-1-[(p-benzyl phenyl)-oxy]-2-cis/trans, 6-cis-dodecadiene is purified by chromatographing on Kieselgel [eluting agent hexane-acetic acid ethyl ester (80:20 parts by volume)].

EXAMPLE 5

5.2 g. of 10,11-eopxy-N,N-diethyl-3,7,11-trimethyl-2-trans, 6-cis-dodecadienoic acid amide are added dropwise at 0° with stirring to a suspension of 1.29 g. of thiourea in 8.45 ml. of 2-N sulfuric acid. The reaction mixture is stirred at 0°–5°C. for 2 hours, then treated with 900 mg. of sodium carbonate in 4 ml. of water and again stirred at room temperature for 2 hours. The mixture is subsequently diluted with water and exhaustively extracted with ether. The extract is washed with a saturated aqueous sodium chloride solution, dried over sodium sulfate and evaporated. The residual 10,11-epithio-N,N-diethyl-3,7,11-trimethyl-2-trans, 6-cis-dodecadienoic acid amide can be purified by chromatographing on Kieselgel [eluting agent hexane-acetic acid ethyl ester (40:60 parts by volume)], $n_D^{20}$ = 1.5135.

By the procedure given above, 10,11-epoxy-N,N-diethyl-3,7,11-trimethyl-2,6-tridecadienoic-1-acid amide is converted to 10,11-epithio-N,N-diethyl-3,7,11-trimethyl-2,6-tridecadienoic-1-acid amide; 10,11-epoxy-N,N-diethyl-7-ethyl-3,11-dimethyl-2,6-tridecadienoic-1-acid amide is converted to 10,11-epithio-N,N-diethyl-7-ethyl-3,11-dimethyl-2,6-tridecadineoic-1-acid amide; and 10,11-epoxy-N,N-diethyl-3,7,10,11-tetramethyl-2,6-dodecadienoic-1-acid amide is converted to 10,11-epithio-N,N-diethyl-3,7,10,11-tetramethyl-2,6-dodecadienoic-1-acid amide.

EXAMPLE 6

To a suspension of 5.35 g. of finely pulverized thiourea in 35 ml. of 2-N-sulfuric acid, 20.7 g. of 10,11-epoxy-3,7,11-trimethyl-2,6-tridecadienoic acid ethyl ester was added dropwise and mixed under constant stirring while cooling with ice. The resulting mixture was allowed to stand for 2 hours under constant stirring while cooling with ice. After this period, a solution containing 3.95 g. of sodium carbonate in 25 ml. of water was added dropwise to the reaction mixture and the mixture was allowed to stand for 1 hour at room temperature. The reaction mixture was poured into water and exhaustively extracted with diethyl ether. The extract was washed with a saturated sodium chloride solution, dried over sodium sulfate and evaporated. The residual 10,11-epithio-3,7,11-trimethyl-2,6-tridecadienoic acid ethyl ester was purified by chromatographing on Kieselgel [eluting agent hexane/diethyl ether (4:1 parts by volume)]. B.P. about 120°C./0.01 mm Hg. (bulb tube distillation); $n_D^{20} = 1.5067$.

EXAMPLE 7

To a suspension of 2.45 g. of finely pulverized thiourea in 16 ml. of 2-N-sulfuric acid, 9 g. of 10,11-epoxy-3,7,11-trimethyl-2-cis/trans, 6-trans-dodecadienoic acid ethyl ester were added dropwise under constant stirring while cooling with ice. The reaction mixture was then allowed to stand under constant stirring for 3 hours at room temperature. After this period, a solution containing 1.8 g. of sodium carbonate in 10 ml. of water was added dropwise to the reaction mixture. The reaction mixture was allowed to stand for 1 hour at room temperature under constant stirring. The reaction mixture was poured into water and exhaustively extracted with diethyl ether. The extract was washed with a saturated aqueous sodium chloride solution, dried over sodium sulfate and evaporated. The residual 10,11-epithio-3,7,11-trimethyl-2-cis/trans, 6-trans-dodecadienoic acid ethyl ester was purified by chromatographing on Kieselgel [eluting agent hexane/ethyl acetate (4:1 parts by volume)]. B.p. was about 115°C./0.001 mm Hg (bulb tube distillation); $n_D^{20} = 1.5068$.

EXAMPLE 8

To a suspension of 1 g. of finely pulverized thiourea in 4 g. of 10,11-epoxy-7-ethyl-3,11-dimethyl-2,6-tridecadienoic acid ethyl ester there was added dropwise 7 ml. of 2-N-sulfuric acid. This addition was accomplished under constant stirring at 0°C. for 2 hours. After this period, a solution containing 750 mg. of sodium carbonate in 3 ml. of water was added and the reaction mixture was allowed to stand for 1 hour at room temperature. The reaction mixture was poured into ice-water and exhaustively extracted with diethyl ether. The extract was washed with a saturated aqueous sodium chloride solution, dried over sodium sulfate and evaporated. The residual, 10,11-epithio-7-ethyl-3,11-dimethyl-2,6-tridecadienoic acid ethyl ester was purified by chromatographing on Kieselgel [eluting agent hexane/diethyl ether (9:1 parts by volume)]. B.p. about 125°C./0.005 mm Hg; (bulb tube distillation); $n_D^{20} = 1.5048$.

EXAMPLE 9

To an ice-cooled suspension of 3.88 g. of finely pulverized thiourea in 15 g. of 10,11-epoxy-3,7,10,11-tetramethyl-dodeca-2, 6-dienoic acid ethyl ester, 25.5 ml. of 2-N-sulfuric acid were added dropwise under constant stirring. The mixture was allowed to stand at room temperature for 3 hours under constant stirring. After this period, a solution containing 2.87 g. of sodium carbonate in 16 ml. of water were added dropwise to the reaction mixture. The reaction mixture was allowed to stand for 1.5 hours at room temperature under constant stirring. The reaction mixture was then poured into ice-water and exhaustively extracted with diethyl ether. The extract was washed with a saturated aqueous sodium chloride solution, dried over sodium sulfate, and evaporated. The residual 10,11-epithio-3,7,10,11-tetramethyldodeca-2,6-dienoic acid ethyl ester was purified by chromatographing on Kieselgel [eluting agent hexane/ethyl acetate (4:1 parts by volume)]. A small sample distilled at about 125°C./0.001 mm Hg. (bulb tube distillation); $n_D^{20} = 1.5081$.

EXAMPLE 10

To a solution of 100 g. of 6,9,10-trimethyl-undeca-5,9-dien-2-one in 2,000 ml. of methylene chloride, there was added, while cooling with ice, 100 g. of m-chloro perbenzoic acid. The resulting mixture was allowed to stand while constantly stirring at room temperature for 1 hour. The resulting mixture was diluted with 1,000 ml. of methylene chloride. The resulting solution was washed with ice-cold 1-N sodium hydroxide solution and with a saturated sodium chloride solution, dried over sodium sulfate and evaporated. The residue was fractionally distilled under high vacuum. There was obtained 9,10-epoxy-6,9,10-trimethyl-undec-5-en-2-one. B.p. 89°–91°C./0.07 mm Hg; $n_D^{20} = 1.4656$.

To a solution of 25 g. of 9,10-epoxy-6,9,10-trimethyl-undec-5-en2-one and 24.8 g. of diethyl phosphonoacetic acid ethyl ester in 160 ml. of absolute ethanol, there was added dropwise while cooling with ice, a solution containing 2.56 g. of sodium in 65 ml. of absolute ethyl alcohol. The mixture was allowed to stand for 14 hours at room temperature and evaporated subsequently under vacuum. The residue was poured into a saturated aqueous sodium chloride solution, exhaustively extracted with diethyl ether, washed with a saturated aqueous sodium chloride solution, dried over sodium sulfate and evaporated. Fractional distillation at high vacuum gave 10,11-epoxy-3,7,10,11-tetramethyl-2,6-dodecadienoic acid ethyl ester. B.p. 110°–113°C./0.01 mm Hg; $n_D^{20} = 1.4792$.

EXAMPLE 11

To a solution containing 7.9 g. of 9,10-epithio-6,10-dimethyl-undec-5-trans-en-2-one and 7.85 g. of diethyl phosphonoacetic acid ethyl ester in 40 ml. of absolute ethanol, there was added, while cooling with ice-water, a solution containing 0.8 g. of sodium in 20 ml. of absolute ethanol. The sodium solution was added dropwise. The mixture was allowed to stand for 4 hours at room temperature while constantly stirring. The resulting mixture was poured into ice-water and exhaustively extracted with diethyl ether. The ether extract was washed with a saturated aqueous sodium chloride solution, dried over sodium sulfate and evaporated. The residual, 10,11-epithio-3,7,11-trimethyl-2-cis/trans,6-trans-dodecadienoic acid ethyl ester was chromatographed on Kieselgel [solvent was hexane/ethyl acetate (4:1 parts by volume)]. B.p. about 115°C.0.001 mm Hg; $n_D^{20} = 1.5069$.

EXAMPLE 12

To a suspension of 31.5 g. of 9,10-epoxy-6,10-dimethyl-undec-5-trans-en-2-one and 11.4 g. of thiourea, 75 ml. of 2-N-sulfuric acid were added dropwise under intensive stirring and cooling with ice. The resultant mixture was allowed to stand for 2 hours under constant stirring while cooling with ice. After this period, a solution of 7.95 g. of sodium carbonate in 35 ml. of water were added dropwise to the resulting mixture. After this, the mixture was allowed to stand for 1 hour at room temperature while constantly stirring. The resulting mixture was poured into a saturated sodium chloride ice-water solution. The reaction mixture was then exhaustively extracted with diethyl ether. The extract was washed with a saturated aqueous sodium chloride solution, dried over sodium sulfate and evaporated. The residual 9,10-epithio-6,10-dimethyl-undec-5-trans-en-2-one was purified by chromatography on Kieselgel [eluting agent hexane/diethyl ether (4:1 parts by volume)], b.p. 85°C/0.001 mm Hg. (bulb tube distillation); $n_D^{20} = 1.4985$.

EXAMPLE 13

To a solution of 7.2 g. of 9,10-epithio-6,9,10-trimethyl-undec-5-cis/trans-en-2-one and 6.73 g. of diethyl phosphonoacetic acid ethyl ester in 30 ml. of absolute ethanol, there was added dropwise with ice-water cooling, a solution of 0.69 g. of sodium in 15 ml. of ethanol. The mixture was allowed to stand under constant stirring under room temperature for 4 hours. After this period, it was poured into ice-water, extracted with diethyl ether. The extract was washed with a saturated aqueous sodium chloride solution, dried over sodium sulfate and evaporated. The residual 10,11-epithio-3,7,10,11-tetramethyl-2,6-dodecadienoic acid ethyl ester was purified by chromatographing on Kieselgel [eluting agent hexane/acetic acid ethyl ester (4:1 parts by volume)]. B.p. 115°C./0.001 mm Hg; (bulb tube distillation); $n_D^{20} = 1.4792$.

EXAMPLE 14

To a suspension of 6.7 g. of thiourea in 22.4 g. of 9,10-epoxy-6,9,10-trimethyl-undec-5-cis/trans-en-2-one, there was added dropwise under intensive stirring 50 ml. of 2-N sulfuric acid. This addition was carried out while cooling with ice. The mixture was allowed to stand under constant stirring and cooling with ice for a period of 2 hours. After this period, a solution of 5.3 g. of sodium carbonate in 20 ml. of water were added dropwise to the reaction mixture. The reaction mixture was allowed to stand for a period of 1.5 hours at room temperature under constant stirring. The resulting solution was poured over ice-water and exhaustively extracted with diethyl ether. The extract was washed with a saturated aqueous sodium chloride solution, dried over sodium sulfate, and evaporated. The residual, 9,10-epithio-6,9,10-trimethyl-undec-5-cis/-trans-en-2-one was purified by chromatographing on Kieselgel [eluting agent hexane/diethyl ether (3:1 parts by volume)]. B.p. 85°C./0.001 mm Hg (bulb tube distillation); $n_D^{20} = 1.5016$.

EXAMPLE 15

To an ice-cold suspension of 2.05 g. of finely pulverized thiourea in 6.2 g. of 10,11-epoxy-3,7,11-trimethyl-dodeca-2-cis/trans,6-trans-dienenitrile, there was added dropwise under constant stirring 13.3 ml. of 2-N-sulfuric acid. The mixture was allowed to stand for 2 hours while cooling with ice and constant stirring. To this mixture there was added a solution of 1.4 g. of sodium carbonate in 6 ml. of water. The resulting mixture was allowed to stand for 1.5 hours at room temperature. The resulting mixture was then poured on ice-water and exhaustively extracted with diethyl ether. The ether extract was washed with a saturated aqueous sodium chloride solution, dried over sodium sulfate and evaporated. The residual 10,11-epithio-3,7,11-trimethyl-dodeca-2-cis/trans,6-trans-dienenitrile was purified by chromatography on Kieselgel [eluting agent hexane/diethyl ether (6:4 parts by volume)]. B.p. about 120°C./0.05 mm Hg (bulb tube distillation); $n_D^{20} = 1.5171$.

The starting material was prepared in the following manner:

To an ice-cold solution of 21 g. of 9,10-epoxy-6,10-dimethyl-undec-5-trans-en-2-one and 18 g. of diethyl phosphonoacetonitrile in 100 ml. of absolute ethanol there was added dropwise under constant stirring a solution of 2.3 g. of sodium in 50 ml. of absolute ethanol. The mixture was allowed to stand for 4 hours at room temperature under constant stirring. After this period, the resultant mixture was evaporated under vacuum. The residue was added to a saturated sodium chloride solution and extracted with diethyl ether. The ether extract was washed with a saturated aqueous sodium chloride solution, dried over sodium sulfate and evaporated. The residual 10,11-epoxy-3,7,11-trimethyl-dodeca-2-cis/trans,6-trans-dienenitrile was obtained from the extract by fractional distillation. B.p. 109°–113°C./0.2 mm Hg; $n_D^{20} = 1.4848$.

By the above procedure 10,11-epoxy-3,7,10,11-tetramethyl-dodeca-2,6-dienenitrile was converted to 10,11-epithio-3,7,10,11-tetramethyl-dodeca-2,6-dienenitrile; 10,11-epoxy-3,7,11-trimethyl-trideca-2,6-dienenitrile was converted to 10,11-epithio-3,7,11-trimethyl-trideca-2,6-dienenitrile; and 10,11-epoxy-7-ethyl-3,11-dimethyl-trideca-2,6-dienenitrile is converted to 10,11-epithio-7-ethyl-3,11-dimethyl-trideca-2,6-dienenitrile.

EXAMPLE 16

Sterilization effect against *Tineola biselliella*.

Short wool strips having an area of 10 cm² were moistened with a solution of the active substance in acetone. The strips were dried at 20°C. For each variation in concentration of the active substance there was a control strip (a strip which was moistened only with acetone). The strips were suspended in a plastic beaker containing 20 freshly hatched clothes moths. The clothes moths were allowed to lay eggs on the strip for a period of 4 days at 25°C. After this period, the strips were transferred to small plastic boxes until the larvae hatched. The untreated strips (control) were suspended in the beaker for 4 days in the same manner as the treated strips. In the following table, sterilization activity of the test compound is given as the percent mortality based upon the control strip. The dosage in the table is given as $10^{-x}$ g activity substance/cm² of wool strips. Thus, dosages of 3 are given as $10^{-3}$ g/cm² of wool strips.

TABLE

| Active Substance | Concentration $10^{-x}$g of Active Substance/ cm² by Dosage | Mortality |
|---|---|---|
| 10,11-epithio-3,7,11-tri-methyl-2,6-tridecadienoic acid ethyl ester | 3 | 80 |
|  | 4 | — |
|  | 5 | 50 |

EXAMPLE 17

4.8 g. of sodium hydride (50% by weight in mineral oil) are washed twice with 50 ml. of absolute hexane and after the addition of 25 ml. of absolute tetrahydrofuran are treated dropwise at 10°–12°C. with 12.6 g. of N,N-diethyl-diethylphosphonoacetamide. The reaction mixture is stirred for 1½ hours at room temperature and subsequently treated dropwise at 10°–12°C. with 11.4 g. of 9,10-epoxy-6,9,10-trimethyl-5-undecen-2-one. The mixture is stirred at room temperature for 20 hours, treated under ice cooling with 10 ml. absolute ethanol in order to destroy excess sodium hydride, poured into a saturated sodium chloride solution and extracted with ether. The combined extracts are washed neutral, dried and evaporated. Pure 10,11-epoxy-N,N-diethyl-3,7,10,11-tetramethyl-2,6-dodecadien-1-oic acid amide is obtained by high vacuum distillation, which boiled at 132°–135°C./0.001 mm Hg; $n_D^{20}$ = 1.4913.

EXAMPLE 18

To an ice-cooled solution of 6.9 g. of 3,7,10,11-tetramethyl-2,6,10-dodecatrienoic acid phenyl ester in 100 ml. of methylene chloride there were added slowly 4.1 g. of an aqueous solution containing 93% by weight of m-chloro-perbenzoic acid. This mixture was stirred for one hour at 0°–3°C. After this period, the mixture was diluted with 200 ml. of diethyl ether and washed with 1N sodium hydroxide and saturated aqueous sodium chloride solution. After washing, the mixture was dried over sodium sulfate and evaporated. The residue was chromatographed on Kieselgel with hexane and diethyl ether solvent mixture (1:1 parts by volume). There resulted pure 10,11-epoxy-3,7,10,11-tetramethyl-2,6-dodecadienoic acid phenyl ester b.p. 150°–155°C./0.001 mmHg (bulb tube distillation); $n_D^{20}$ = 1.5207.

EXAMPLE 19

19.4 g. of 3,7,10,11-tetramethyl-2,6,10-dodecatrienoic acid ethyl ester were mixed into 240 ml. of a 0.5N, 50% by weight water alcaline solution. This mixture was allowed to stand for 24 hours at 40° while stirring. The mixture was poured over ice-water and extracted with diethyl ether. The water alcoholic solution was then acidified with ice-cold 1N hydrochloric acid and then extracted with diethyl ether. The resulting extract was washed with saturated aqueous sodium chloride solution and dried over sodium sulfate. Upon distillation there resulted 3,7,10,11-tetramethyl-2,6,10-dodecatrienoic acid: b.p. 123°C/0.01 mmHg; $n_D^{20}$ = 1.5024.

EXAMPLE 20

To 10 g. of 3,7,10,11-tetramethyl-2,6,10-dodecatrienoic acid and 3.8 ml. of absolute pyridine in 80 ml. of absolute diethyl ether, 5.4 ml. of thionyl chloride were added dropwise under cooling. The reaction mixture was continually stirred for 75 minutes at 0°–2°C. Thereafter, the resulting mixture was filtered with precipitated pyridine hydrochloride and the filtrate was evaporated under vacuum. After evaporation, the residue was mixed into 20 ml. of absolute benzene. To this reaction mixture there was added dropwise 3.9 g. of phenol and 3.8 ml. of absolute pyridine in 170 ml. of absolute benzene. This addition was carried out dropwise. The resulting reaction mixture was continually stirred at room temperature for 2 hours. After this period, the reaction mixture was poured over dilute ice-cold hydrochloric acid and exhaustively extracted with benzene. The combined benzene extracts were diluted with an aqueous sodium bicarbonate solution. After this, the dilute extract is washed with a saturated sodium chloride solution and dried over sodium sulfate and evaporated. By chromatography on Kieselgel with hexane/diethyl ether (95:5 parts by volume) there is obtained pure 3,7,10,11-tetramethyl-2,6,10,-dodecatrienoic acid phenyl ester; b.p. 135°–140°C./0.001 mmHg (bulb tube distillation).

EXAMPLE 21

1.2 g. of sodium hydride (50% by weight suspension in mineral oil) was washed twice with hexane. After discarding the hexane washes, the 1.2 g. of sodium hydride was suspended in 5 ml. of absolute tetrahydrofuran. To the tetrahydrofuran suspension there were added dropwise under ice-cooling, 6.3 g. of 10,11-epoxy-3,7,10,11-tetramethyl-2,6-dodecadien-1-ol in 10 ml. of absolute tetrahydrofuran. The resulting reaction mixture was stirred at room temperature for one hour. Afterward, to the reaction mixture there were first added 6 g. of ethyliodide and then added 10 ml. of hexamethyl phosphoric acid triamide. The 10 ml. of hexamethyl phosphoric acid triamide were added dropwise to the reaction mixture. After standing one hour under stirring at room temperature, the reaction mixture was mixed with ice-water and exhaustively extracted with petroleum ether; b.p. 40°–45°C. The combined petroluem ether extracts were washed with an aqueous saturated sodium chloride solution and dried over sodium sulfate and evaporated. By chromatography on Kieselgel with hexane/diethyl ether (9:1 parts by volume) there were obtained 10,11-epoxy-1-ethoxy-3,7,10,11-tetramethyl-2,6-dodecadiene; b.p. 100°C./0.001 mmHg (bulb tube distillation; $n_D^{20}$ = 1.4731.

EXAMPLE 22

A mixture containing 111 g. of 1-bromo-3,7,10,11-tetramethyl-2,6,10-dodecatriene and 72.5 g. of water-free calcium acetate were refluxed for 16 hours in 840 ml. of water-free acetone. After this period, the mixture was filtered. The filtrate was dried and then chromatographed on Kieselgel with a hexane/diethyl ether mixture (9:1 parts by volume). There was obtained 1-acetoxy-3,7,10,11-tetramethyl-2,6,10-dodecatriene, b.p. 103°–104°C./0.003 mmHg; $n_D^{20}$ = 1.4845.

EXAMPLE 23

To a homogeneous solution containing 39 g. of 1-acetoxy-3,7,10,11-tetramethyl-2,6,10-dodecatriene in 365 ml. of absolute tetrahydrofuran and 56 ml. of water there were added portionwise, under cooling, with ice, 27.5 g. of N-bromosuccinimide. After this addition, the mixture was allowed to stand for 3 hours at 0°–3°C. under constant stirring. The reaction solution was then mixed with water and then exhaustively extracted with hexane. The combined hexane extracts were washed with water, dried over sodium sulfate and evaporated. By chromatography on Kieselgel with hexane-ethyl acetate (3:2 parts by volume) there was obtained 1-acetoxy-10-bromo-(or hydroxy)-11-hydroxy-(or bromo)-3,7,10,11-tetramethyl-2,6-dodecadiene. This compound was dried under high vacuum; $n_D^{20}$ = 1.5070.

EXAMPLE 24

To an ice-cold solution containing 36.2 g. of 1-acetoxy-10-bromo-(or hydroxy)-11-hydroxy-(or bromo)-3,7,10,11-tetramethyl-2,6-dodecadiene in 100 ml. of absolute methanol there was added in about 30 minutes a solution containing 4.45 g. of sodium in 100 ml.

of absolute methanol. The sodium solution was added dropwise to the methanol. After this addition, the reaction mixture was allowed to stand under constant stirring for 5 hours at room temperature. After this, the reaction mixture was mixed with a saturated aqueous sodium chloride solution and then exhaustively extracted with petroleum ether (b.p. 40°–45°). The combined petroleum ether extracts were washed with a saturated aqueous sodium chloride solution, dried over sodium sulfate and evaporated. By chromatography with Kieselgel utilizing hexane-diethyl ether (1:1 parts by volume), there was obtained pure 10,11-epoxy-3,7,10,11-tetramethyl-2,6-dodecadien-1-ol, b.p. 106°–109°C./0.04 mmHg; $n_D^{20} = 1.4871$.

EXAMPLE 25

To a solution containing 2.3 g. of sodium in 100 ml. of absolute methanol, there were added 41.8 g. of 1-acetoxy-3,7,10,11-tetramethyl-2,6,10-dodecatriene. The reaction mixture was allowed to stand for 16 hours at room temperature under constant stirring. The reaction mixture was then evaporated under vacuum and poured onto a saturated aqueous sodium chloride solution. After this, the reaction mixture was exhaustively extracted with petroleum ether (b.p. 40°–45°). The combined petroleum ether extracts were dried over sodium sulfate and evaporated. Distillation produced 3,7,10,11-tetramethyl-2,6,10-dodecatrien-1-ol, b.p. 92-93°C./0.02 mmHg; $n_D^{20} = 1.4947$.

EXAMPLE 26

To 65 g. of 3,7,10,11-tetramethyl-2,6,10-dodecatrienoic acid ethyl ester in 270 ml. of absolute benzene there was added in a period of one hour under ice cooling, 68 ml. of a 70% by weight benzene solution of sodium dihydro-bis-(2-methoxyethoxy-aluminate). This addition was carried out dropwise. After this addition, the reaction mixture was allowed to stand for one hour at room temperature under constant stirring. The reaction solution is broken up by the addition of water while it is cooled with ice. After the addition of water, the reaction mixture is filtered and poured over a saturated aqueous sodium chloride solution. The resulting reaction mixture is then exhaustively extracted with benzene. The combined benzene extracts are washed several times with water, dried over sodium sulfate and evaporated. Distillation yields pure 3,7,10,11-tetramethyl-2,6,10-dodecatrien-1-ol, b.p. 94°–96°C.10.03 mmHg; $n_D^{20} = 1.4946$.

EXAMPLE 27

To 23.6 g. of 3,7,10,11-tetramethyl-2,6,10-dodecatrien-1-ol in 500 ml. of methylene chloride, there was added under ice cooling 22.6 g. of m-chloroperbenzoic acid (79% by weight water solution). This addition was carried out portionwise. After this addition, the mixture was agitated for 2 hours at 0°C. After this period, the reaction mixture was diluted with 1,000 ml. of diethyl ether and washed with ice cold 1N aqueous sodium hydroxide and a saturated sodium chloride solution. After washing, the reaction mixture was dried over sodium sulfate and evaporated. By chromatography on Kieselgel, there was obtained 10,11-epoxy-3,7,10,11-tetramethyl-2,6-dodecadien-1-ol, b.p. 104°–107°C./0.02 mmHg; $n_D^{20} = 1.4867$.

EXAMPLE 28

To a solution containing 15.3 g. of 1-methoxy-3,7,10,11-tetramethyl-2,6,10-dodecatriene in 150 ml. of methylene chloride there was added portionwise under ice cooling and stirring, 12.6 g. of m-chloroperbenzoic acid, (93% by weight of an aqueous mixture). After the addition, the reaction mixture was allowed to stand for 1.5 hours at 0°C. under constant stirring. The reaction mixture was then diluted with 300 ml. of diethyl ether and washed with ice cold 1N sodium hydroxide and a saturated sodium chloride aqueous solution. The washed reaction mixture was dried over sodium sulfate and evaporated. By chromatography on Kieselgel with hexane/diethyl ether (4:1 parts by volume) and followed by distillation one obtained pure 10,11-epoxy-1-methoxy-3,7,10,11-tetramethyl-2,6-dodecadiene; b.p. 92°–94°C./0.04 mmHg; $n_D^{20} = 1.4746$.

EXAMPLE 29

34.5 g. of sodium were dissolved in 3,000 ml. of liquid ammonia. Dry pure acetylene was introduced into the resulting blue solution until the solution was a clear color. After this acetylene addition was continued while 312 g. of 6,9,10-trimethyl-5,9-undecadien-2-one in 2250 ml. of absolute inert diethyl ether was added dropwise. This addition was carried out in 30 minutes at a temperature of −45°C. to −40°C. After this addition, the resulting reaction mixture was stirred for 18 hours at −32°. 240 g. of ammonium chloride was added portionwise and the ammonia was evaporated under mild warming. Thereafter, there was added 2,250 ml. of water and the ether layer was discarded. The resulting water solution was exhaustively extracted with diethyl ether and the combined ether extracts were washed first with 0.5N sulfuric acid and then with a saturated sodium chloride. The resulting mixture was then dried over sodium sulfate and evaporated to yield 3,7,10,11-tetramethyl-6,10-dodecadien-1-yn-3-ol, b.p. 86°–91°C./0.02 mmHg.

Example 30

274.5 g. of 3,7,10-tetramethyl-6,10-dodecadien-1-yn-3-ol was mixed into 710 ml. of petroleum ether (boiling point range 80°–105°C.) and 6.25 ml. quinoline. To this reaction mixture there was added 7.66 g. of the Lindlar Catalyst [Helv. Chim. Acta, 35, 446 (1952)]. All of these reaction ingredients were shaken together in a hydrogen atmosphere. During this shaking, cooling with ice water became necessary at times. The hydrogenation was carried out until 1 mole of hydrogen was taken up by the reaction mixture. After this period, the hydrogenation was stopped, the catalyst was filtered from the reaction medium, and the filtered reaction medium was washed with a small amont of petroleum ether. The petroleum ether solution was washed first with dilute sulfuric acid, then with water, then with a dilute aqueous bicarbonate solution and finally with water. After washing, the reaction medium was dried under sodium sulfate and the petroleum ether was evaporated. The residue was vacuumed distilled to produce 3,7,10,11-tetramethyl-1,6,10-dodecatrien-3-ol, b.p. 111°–112°C./0.35 mmHg.

EXAMPLE 31

To a solution containing 223.9 g. of 3,7,10,11-tetramethyl-1,6,10-dodecatrien-3-ol in 570 ml. of hexane and 22.2 ml. of pyridine there was added dropwise at −7°C. over a period of two hours, 112 g. of phosphorous tribromide in 125 ml. of hexane. The resulting mixture was stirred for 30 minutes. After this, the reaction mixture was poured onto ice water and the reaction mixture was allowed to stand under constant stirring for 30 minutes. After 30 minutes, the reaction mixture was diluted with 1,000 ml. of hexane and the water layer was separated and the hexane layer was washed with water, aqueous sodium bicarbonate and finally with water. After washing, the hexane solution was dried over sodium sulfate and evaporated. There resulted 1-bromo-3,7,10,11-tetramethyl-2,6,10-dodecatriene.

EXAMPLE 32

To a solution containing 8.6 g. of sodium dissolved in 172 ml. of absolute methanol, then was added dropwise over a period of 30 minutes, 111 g. of 1-bromo-3,7,10,11-tetramethyl-2,6,10-dodecatriene. The reaction mixture was refluxed for 16 hours. After reflux, the reaction mixture was dried under vacuum and poured onto ice water. The resulting mixture was exhaustively extracted with petroleum ether (b.p. 40°–45°C.). The combined petroleum ether extracts were washed neutral with saturated aqueous sodium chloride solution, dried over sodium sulfate and evaporated. By chromatography on Kieselgel with hexane/diethylether (95:5 parts by volume) and distillation, there was obtained 1-methoxy-3,7,10,11-tetramethyl-2,6,10-dodecatriene, b.p. 87°-88°C./0.02 mmHg; $n_D^{20}$ = 1.4826

EXAMPLE 33

To an ice cold solution containing 10.4 g. of 3,6,7-trimethyl-1-[3,4-(methylenedioxy)-phenoxy]-2,6-octadiene in 100 ml. of methylenechloride, 7 g. of m-chloroperbenzoic acid were added portionwise. After this addition, the reaction mixture was allowed to stand for 2 hours at 0° to 3°C. under constant stirring. After this period, the reaction mixture was diluted with 250 ml. of diethylether, and washed with ice cold 1N sodium hydroxide and saturated aqueous sodium chloride solution. After washing, the reaction mixture was dried over sodium sulfate and evaporated. By chromatography on Kieselgel with hexane-diethylether (4:1 parts by volume) and distillation under vcuum, there was obtained pure 6,7-epoxy-3,6,7-trimethyl-1-[3,4-(methylenedioxy)-phenoxy]-2-octene; b.p. 120°–122°C./0.004 mmHg; $n_D^{20}$ = 1.5277.

EXAMPLE 34

26 g of 1-bromo-3,6,7-trimethyl-2,6-octadiene, 13 g of 3,4-methylenedioxy-phenol [sesamol] and 20.75 g of finely pulverized calcium carbonate were refluxed for 68 hours in 100 ml of acetone. After reflux the reaction mixture was filtered and the acetone solution was evaporated. By chromatography on Kieselgel with hexane-diethylether (4:1 parts by volume) and distillation under vacuum there was obtained pure 3,6,7-trimethyl-1-[3,4-(methylenedioxy)-phenoxy]-2,6-octadiene, b.p. 114°−117°C/0.002 mmHg; $n_D^{20}$ = 1.5352.

EXAMPLE 35

To an ice cold solution containing 9.85 g. of 9,10-epoxy-6,9,10-trimethyl-undec-5-en-2-one and 7.3 g. of diethyl phosphono acetonitrile in 50 ml. of ethyl alcohol, there was added dropwise a solution containing 1.1 g. of sodium in 25 ml. of ethyl alcohol. After the addition, the reaction mixture was allowed to stand 2 hours at room temperature. After this period, the reaction mixture was dried under vacuum and poured onto ice water. After this, the reaction mixture was exhaustively extracted with diethyl ether. The combined ether extracts were washed with an aqueous saturated sodium chloride solution, dried under sodium sulfate and evaporated. By chromatography on Kieselgel with hexane-ethyl acetate (1:1 parts by volume) was obtained pure 10,11-epoxy-3,7,10,11-tetramethyl-2,6-dodecadiene nitrile, b.p. 108°–111°C./0.005 mmHg; $n_D^{20}$ = 1.4861.

EXAMPLE 36

895 mg. of sodium hydride were washed twice with hexane and suspended in 50 ml. of N,N-dimethylformamide. To this suspension there was added dropwise, at room temperature, 4.7 g. of 10,11-epoxy-3,7,10,11-tetramethyl-2,6-dodecadien-1-ol. After this addition, the mixture was allowed to stand for one hour under constant stirring. Following this period, there was added 2.55 g. of 1-chloro-2-diethylamino-ethane. The reaction mixture was then stirred under an atmosphere of argon gas for 16 hours while maintaining the inner temperature of the rection mixture at 50°C. After this period, the reaction mixture was poured onto ice water and exhaustively extracted with petroleum ether (b.p. 40°–45°C.). Combined petroleum ether extracts were washed with an aqueous saturated sodium chloride solution, dried under sodium sulfate and evaporated. By chromatography on basic aluminum oxide (activity II) with hexane-diethyl ether (3:1 parts by volume), one obtains pure (2-diethylamino-ethyl)-10,11-epoxy-3,7,10,11-tetramethyl-2,6-dodecadienyl)-ether; b.p. 115°C./0.01 mmHg (bulb tube distillation); $n_D^{20}$ = 1.4778.

EXAMPLE 37

Ovicidal action with Ephestia kuhniella (A) and Tineola biselliella (B)

Roundels (10 cm²) of cotton material are drenched with acetonic solution of the active substance and cautiously dried. For each variant, 30–60 freshly laid eggs of the meal moth are placed on the roundels and brought to hatching in a small cage of plastic at 25°C. and high humidity.

The action of the substance manifests itself in an earlier or later dying off of the embryos in the egg or on hatching.

The results are expressed in % egg mortality. The dosage is stated in: $10^{-x}$g of active substance/cm² of material.

Dosage 3 accordingly signifies: $10^{-3}$ g/cm²

| Preparation | Concn. $10^{-x}$ act.subst/cm² (dosage) | Egg mortality in% A | B |
|---|---|---|---|
| 10,11-Epoxy-3,7,10,11-tetramethyl-2,6-dodecadienoic acid ethyl ester | 3 | 100 | 100 |
| | 4 | 100 | x |
| | 5 | 86 | x | x = not tested.
act.subst. = active substance

EXAMPLE 38

Dysdercus cingulatus : Sterilant action

Filter paper strips of 90 cm² area are uniformly drenched with acetonic solution of the active substance and allowed to dry. For each variant, a plastic beaker is lined with the filter paper and there are placed therein 3–4 pairs each of freshly moulted imagos which are fed with cotton seed and watered with water. Egg-laying commences after a few days. The eggs are removed daily and brought into vessels suitable for the hatching of the larvae.

The action of the substance manifests itself in the dying off of the embryos in the egg or of the larvae shortly after hatching (the viability of the larvae is only tested up to the 2nd larval stage). The results are expressed in % egg mortality compared to the controls.

The dosage is stated in $10^{-x}$ g of active substance/cm² of filter paper.

Dosage 5 accordingly signifies: $10^{-5}$ g/cm²

| Preparation | Concn. $10^{-x}$g act. subst./ cm² (dosage) | Sterilant action in % |
|---|---|---|
| 10,11-Epoxy-3,7,10,11-tetramethyl-2,6-dodeca-dienoic acid ethyl ester | 3 | 100 |
|  | 4 | 100 |
|  | 5 | 100 |

We claim:

1. A method for controlling insects comprising applying to materials to be protected a composition containing a compound of the formula

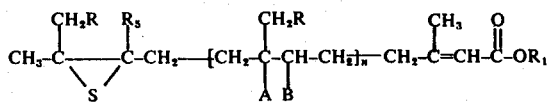

wherein A and B are hydrogen or taken together form a carbon to carbon bond or a sulfur bridge; R is hydrogen or lower alkyl; R₁ is selected form the group consisting of hydrogen, lower alkyl and

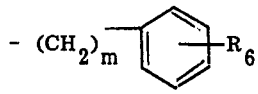

R₅ is methyl or hydrogen, R₆ is hydrogen, lower alkyl, hydroxy, lower alkoxy or halogen, m is an integer of from 0 to 1; and n is an integer from 0 to 1; and an inert carrier, said compound being present in said composition in an insecticidally effective amount sufficient to provide 0.01 percent to 1.0 percent of said compound on said material to be protected.

2. The composition of claim 1 wherein said compound is (10,11-epithio-3,7,11-trimethyl-2-cis/trans,6-cis-dodecadienyl) methyl ether.

3. The composition of claim 1 wherein said compound is (α-phenyl-p-tolyl) (10,11-epithio-3,7,11-trimethyl-2-cis/trans, 6-cis-dodecadienyl) ether.

4. A composition for controlling insects comprising an insecticidally effective amount of a compound of the formula:

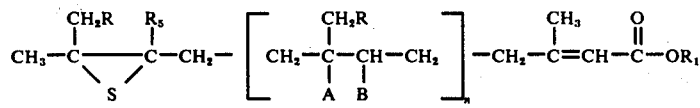

wherein A and B are hydrogen or taken together form a carbon to carbon bond or a sulfur bridge: R is hydrogen or lower alkyl; R₁ is selected from the group consisting of hydrogen, lower alkyl and

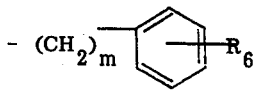

R₅ is methyl or hydrogen, R₆ is hydrogen, lower alkyl, hydroxy, lower alkoxy or halogen, m is an integer of from 0 to 1, and n is an integer from 0 to 1; and an inert carrier.

5. The method of claim 1 wherein said compound is (10,11-epithio-3,7,11-trimethyl-2-cis/trans,6-cis-dodecadienyl) methyl ether.

6. The method of claim 1 wherein said compound is (α-phenyl-p-tolyl) (10,11-epithio-3,7,11-trimethyl-2-cis/trans,6-cis-dodecadienyl) ether.

* * * * *

UNITED STATES PATENT AND TRADEMARK OFFICE
CERTIFICATE OF CORRECTION

PATENT NO. : 3,983,243
DATED : September 28, 1976
INVENTOR(S) : Albert Pfiffner and Ulrich Schwieter It is certified that error appears in the above–identified patent and that said Letters Patent are hereby corrected as shown below:

Column 30, line 16, "1" should be: 4

Column 30, line 19, "1" should be: 4

Signed and Sealed this

Eighth Day of November 197

[SEAL]

Attest:

RUTH C. MASON
*Attesting Officer*

LUTRELLE F. PARKER
*Acting Commissioner of Patents and Trademar*